United States Patent [19]
Lang, Jr. et al.

[11] 4,115,097

[45] Sep. 19, 1978

[54] PYRAZOLYLTRIAZOLE HERBICIDES

[75] Inventors: Stanley Albert Lang, Jr., Pomona, N.Y.; Bryant Leonidas Walworth, Pennington, N.J.

[73] Assignee: American Cyanamid Company, Stamford, Conn.

[21] Appl. No.: 791,460

[22] Filed: Apr. 27, 1977

Related U.S. Application Data

[62] Division of Ser. No. 619,982, Oct. 6, 1975.

[51] Int. Cl.$^2$ .................. A01N 9/22; C07D 55/06
[52] U.S. Cl. ................................ 71/92; 71/66; 260/308 R
[58] Field of Search ............................ 71/92

[56] References Cited

U.S. PATENT DOCUMENTS

| | | | |
|---|---|---|---|
| 3,326,662 | 6/1967 | Toyasoto et al. | 71/92 |
| 3,701,784 | 10/1972 | Seidel et al. | 71/92 |
| 3,914,223 | 10/1975 | Seidel et al. | 71/92 |
| 4,017,298 | 4/1977 | Cross et al. | 71/92 |

*Primary Examiner*—Catherine L. Mills
*Attorney, Agent, or Firm*—H. G. Jackson

[57] ABSTRACT

The invention is novel 4-(pyrazolyl)-4H-1,2,4-triazoles, the preparation thereof including their salts, and a method for controlling undesirable plant species therewith.

5 Claims, No Drawings

PYRAZOLYLTRIAZOLE HERBICIDES

This is a division of application Ser. No. 619,982, filed Oct. 6, 1975, pending.

SUMMARY OF THE INVENTION

The invention is compounds of the formula:

wherein $R_1$ is hydrogen, alkyl $(C_1-C_3)$, benzyl, acyl $(C_2-C_4)$ or N-alkyl $(C_1-C_3)$ carboxamido; $R_2$ is hydrogen, methyl or phenyl; $R_3$ is methyl or wherein X is hydrogen, halogen, alkyl $(C_1-C_3)$ or trifluoromethyl; or acid addition salts of the compounds. The invention includes a method for preparing the compounds and a method for controlling undesirable plant species therewith.

BACKGROUND OF THE INVENTION

1. Field of the Invention

The invention pertains to herbicidal pyrazolyltriazole.

2. Description of the Prior Art

Prior art is as follows. Triazolylpyrazoles, Fedotova, A. P.; Kazymov, A. V.; Shchelkina, E. P. (All Union Scientific-Research Institute of the Photographic Chemical Industry) U.S.S.R. 245, 554 (1969). Heterocyclic Compounds from Urea Derivatives, Kurzer, Frederick and Douraghi-Zadeh, K.; J. Chem. Soc. p. 3912–3922 (1965). Heterocyclic Compounds from Urea Derivatives, Kurzer, Frederick and Douraghi-Zadeh, K.; J. Chem. Soc. P. 4448–4455 (1965). Syntheses and Reactions of 5-Alkyl-4-Amino-3-Hydrazino-s-Triazoles, Takimoto, H. H., Denault, G. C. and Hotta, S.; J. Org. Chem. 30:711–713 (1965).

DESCRIPTION OF THE PREFERRED EMBODIMENTS

4-Pyrazolyl-4H-1,2,4-triazole exists as a tautomeric isomer, as illustrated below:

Structure determinations by x-ray crystallographic analysis indicate that the two tautomers I*a* and I*b* are present in an approximately 50:50 ratio.

The novel derivatives of the above compound (I*a*⇌I*b*), comprise the compounds of the present invention and are graphically illustrated as follows:

Since the tautomers II*a*⇌II*b* also exist in approximately 50:50 ratios (as confirmed by x-ray crystallographic analysis), numerical structure assignment is arbitrary, and in the present application will be based on structure II*b*, with the proviso, that if the hydrogen on the pyrazole ring is replaced by an alkyl group then it will be indicated if the compound obtained is an isomeric mixture.

The compounds of the invention are illustrated and defined as follows:

wherein $R_1$ is hydrogen, alkyl $(C_1-C_3)$, benzyl, acyl $(C_2-C_4)$ or N-alkyl $(C_1-C_3)$ carboxamido; $R_2$ is hydrogen, methyl or phenyl; $R_3$ is methyl or wherein X is hydrogen, halogen, alkyl $(C_1-C_3)$ and trifluoromethyl; and salts thereof.

The invention also relates to a method for controlling undesirable plant species with the compounds III, above. The pyrazolyltriazole compounds of the invention can be prepared by several procedures. One procedure, hereinafter referred to as procedure A, comprises, reacting an arylcyanoacetaldehyde (1) or an arylcyanoketone (2) with formylhydrazine in a molar ratio of 1:2 but preferably with an excess of formylhydrazine (1:2.5 to 1:3.0 molar ratio) in a melt at elevated temperatures of from about 150° C. to 250° C. and preferably 160° C. to 190° C. and a reaction time from about 1 hour to about 5 hours. The reaction scheme of procedure A, reacting arylcyanoacetaldehyde (1) or arylcyanoketone (2) with formylhydrazine, is graphically illustrated as follows:

Procedure A

-continued

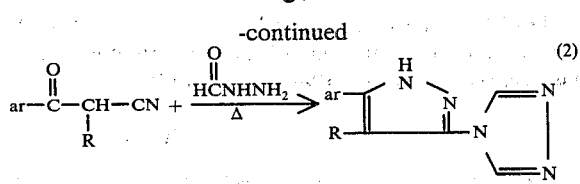

On completion of the reaction the melt is triturated with a mixture of water and a chlorinated hydrocarbon to remove the unreacted starting materials which may be present. The isolated crude product may then be further purified if necessary by standard laboratory procedures, such as crystallizations, precipitations, chromatography and the like, all well known to the practitioners of the art.

Another procedure which may be used to prepare the pyrazolyltriazole compounds of the invention, hereinafter referred to as procedure B, comprises, reacting a substituted 3-aminopyrazole with a sym-diformylhydrazine in a molar ratio of 1:1 to 1:3 in a high boiling polar solvent, such as ethylene glycol, propylene glycol, diethylene glycol, diethylene glycol monomethylether and the like at temperatures from about 100° C. to 250° C. and preferably 150° C. to 190° C. Procedure B is graphically illustrated as follows:

Procedure B

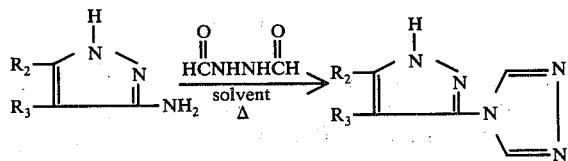

On completion of the reaction the product may be isolated and purified by standard laboratory procedures, such as filtration, precipitation, crystallization, chromatography and the like.

The acid addition salts of the compounds of the present invention may be prepared by treating said compounds in an alcohol ($C_1$–$C_3$) with the appropriate acid, evaporating the thus formed solution to dryness and recovering the desired acid addition salt. Illustrative of the acids which are suitable for use in the present invention may be mentioned for example, acids such as hydrochloric acid, hydrobromic acid, hydroiodic acid, sulfuric acid, hydrogen sulfate, methyl sulfate, nitric acid, phosphoric acid, perchloric acid, alkanoic ($C_2$–$C_4$) acid, benzene sulfonic acid, p-toluene sulfonic acid and the like.

If desired, the compounds of the present invention may be acylated by standard laboratory procedures using acid chlorides, or anhydrides such as acetyl chloride, propionyl chloride, benzoyl chloride, acetic anhydride, propionic anhydride and the like. The compounds of the present invention may also be alkylated by the alkyl halides, alkyl sulfates, alkyl toluenesulfonates and the like by standard laboratory procedures.

Among the compounds which can be prepared by one or both of the above procedures are:

4-(4-Phenyl-3-pyrazolyl)-4H-1,2,4-triazole;
4-(4-Phenyl-3-pyrazolyl)-b 4H-1,2,4-triazole hydrochloride;
4-(4-Phenyl-3-pyrazolyl)-4H-1,2,4-triazole nitrate;
4-(1-Acetyl-4-phenyl-3-pyrazolyl)-4H-1,2,4-triazole;
4-(1-Acetyl-4-phenyl-3-pyrazolyl)-4H-1,2,4-triazole hydrochloride;
4-(4-Phenyl-1-propionyl-3-pyrazolyl)-4H-1,2,4-triazole
4-[1(2)-N-Methylcarboxamido-4-phenyl-3(5)pyrazolyl]-4H-1,2,4-triazole;
4-[1(2)-Methyl-4-phenyl-3(5)-pyrazolyl]-4H-1,2,4-triazole;
4-[1(2)-Benzyl-4-phenyl-3(5)-pyrazolyl]-4H-1,2,4-triazole;
4-(4-o-Tolyl-3-pyrazolyl)-4H-1,2,4-triazole;
4-(4-o-Tolyl-3-pyrazolyl)-4H-1,2,4-triazole hydrochloride;
4-(4-m-Tolyl-3-pyrazolyl)-4H-1,2,4-triazole;
4-(4-m-Tolyl-3-pyrazolyl)-4H-1,2,4-triazole hydrochloride;
4-(4-m-Chlorophenyl-3-pyrazolyl)-4H-1,2,4-triazole;
4-(4-m-Chlorophenyl-5-methyl-3-pyrazolyl)-4H-1,2,4-triazole;
4-(4-p-Chlorophenyl-3-pyrazolyl)-4H-1,2,4-triazole;
4-(4-m-Fluorophenyl-3-pyrazolyl)-4H-1,2,4-triazole;
4-(4-p-Fluorophenyl-3-pyrazolyl)-4H-1,2,4-triazole;
4-[4-($\alpha,\alpha,\alpha$-Trifluoro-m-tolyl)-3-pyrazolyl]-4H-1,2,4-triazole;
4-(4-Methyl-5-phenyl-3-pyrazolyl)-4H-1,2,4-triazole;
4-(4-Methyl-5-phenyl-3-pyrazolyl)-4H-1,2,4-triazole hydrochloride.

The compounds of the present invention as represented and defined by formula III above are highly effective herbicidal agents. They are particularly effective as selective preemergence herbicides applied at a rate between 0.11 kg and 11.2 kg per hectare and preferably from 0.56 kg to 5.6 kg per hectare of active compound, and will control wild oats, crabgrass, foxtail, and barnyardgrass, and broadleaf weeds such as mustard, pigweed, velvetleaf and morningglory in the presence of crops such as corn, cotton, soybeans and rice.

The compounds of the present invention, as represented and defined by formula III above are also effective as postemergence herbicides applied to the foliage of undesirable plants at a rate between about 1.1 kg to 11.2 kg per hectare, and preferably from 1.1 kg to 5.6 kg per hectare. Used as postemergence herbicides, the compounds of the present invention display activities similar to those described under preemergence, i.e. at lower rates (as described above) they selectively control wild oats, crabgrass, foxtail, barnyardgrass, mustard, pigweed, velvetleaf and morningglory in the presence of crops such as corn, cotton, soybean and rice.

The compounds of the present invention, when applied at high levels, will act as broad spectrum herbicides and thus may be used to eliminate all vegetation where this may be desirable.

For application of the formula III compounds and their salts as pre- and postemergence herbicides, the compounds or their salts are generally formulated as herbicidal compositions by admixing a suitable adjuvant with a herbicidally effective amount of these compounds or their salts. Suitable adjuvants include one or more solid or liquid carriers, diluents and formulation aids, particularly surfactants.

The active compounds may be formulated as dusts, dust concentrates, granules, prills, wettable powders or emulsifiable concentrates.

Dusts are readily prepared by grinding together about 1 to 25% by weight of the active agent from about 99 to 75% by weight of a solid diluent such as kaolin, attapulgite, diatomaceous earth, or the like. Dust concentrates are prepared in a similar fashion excepting that about 25 to 95% by weight of the active agent is ground about 75 to 5% by weight of the diluent. Granules or prills may be prepared from the above formulations by standard industrial methods.

Wettable powders are prepared in the same manner as the dust concentrates excepting that about 1 to 5% by weight of a dispersing agent such as sodium lignosulfonate, or the sodium salt of condensed naphthalene sulfonic acid is blended with the mixture and about 1 to 5% of a surfactant, such as polyoxyethylene ethanol is also blended with the formulation. In practice the powder is mixed with water and applied to the plant foliage as an aqueous spray.

Emulsifiable concentrates are prepared by dissolving from 15 to 70% of the compound in 85 to 30% of a water-miscible solvent, such as water itself or another polar water-miscible solvent, such as 2-methoxy ethanol, methanol, propylene glycol, diethylene glycol, diethylene glycol monomethyl ether, formamide, and methylformamide, wherein said concentrates contain 1 to 5% of a surfactant, such as TWEEN ® 20, a polyoxyethylene sorbitan monolaurate surfactant by Atlas Chemical Industries, or the like. Application of the material is made by adding a predetermined quantity to a spray tank and applying the concentrate as such or in combination with an additional quantity of water or other polar solvent as a liquid spray.

The present invention is further illustrated by the examples set forth below. These examples are provided only by way of illustration and are not intended to be limiting on the invention.

EXAMPLE 1

Preparation of 4-(4-phenyl-3-pyrazolyl)-4H-1,2,4-triazole, Method A

An integral mixture of β-hydroxy-α-phenylacrylonitrile (5 g) and formylhydrazine (10 g ) is heated in an oil bath at 170° C to 180° C. The melt is stirred and heated for 3 hours. It is then cooled, water (50 ml) and chloroform (50 ml) is added and the mixture stirred. The solid is collected by filtration and recrystallized from a mixture of methanol/dimethylsulfoxide, m.p. 271° C to 274° C (dec).

EXAMPLE 2

Preparation of 4-(4-phenyl-3-pyrazolyl)-4H-1,2,4-triazole, Method B

A slurry of 3-amino-4-phenylpyrazole (1.6 g, 0.01 mole) and sym-diformylhydrazine (2.2 g, 0.025 mole) in ethylene glycol (10 ml) is prepared and heated slowly to 80° C, at which point a clear solution is obtained. Heating is continued to 150° C and the solution held at 150° C to 180° C for 3 hours. The mixture is then cooled to 60° C and filtered to give 1.3 g of product. A second fraction of 0.3 g is obtained by diluting the filtrate with water. Both fractions are identical to the product of Example 1. The combined yield is 76%.

EXAMPLE 3

Preparation of 4-(4-phenyl-3-pyrazolyl)-4H-1,2,4-triazole hydrochloride

A suspension of 4-(4-phenyl-3-pyrazolyl)-4H-1,2,4-triazole (1.75 g) in methanol (25 ml) and water (10 ml) is stirred and concentrated hydrochloric acid until a clear solution is obtained. The solvent is removed and the residue recrystallized from methanol/ether at −10° C Yield 1.7 g (90%), mp. 210° C to 216° C (dec).

EXAMPLE 4–16

By the procedure of Example 1, (Method A) the following compounds, and by the procedure of Example III their acid addition salts, are prepared corresponding to formula III.

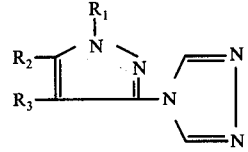

Table I

| Experiment No. | $R_1$ | $R_2$ | $R_3$ | Acid | m.p. |
|---|---|---|---|---|---|
| 4 | H | H | phenyl | HNO$_3$ | 158° C–160° C |
| 5 | H | H | p-Chlorophenyl | | 257° C–260° C |
| 6 | H | H | m-Chlorophenyl | | 203° C–205° C |
| 7 | H | H | p-Fluorophenyl | | |
| 8 | H | H | m-Fluorophenyl | | 235° C–238° C |
| 9 | H | H | o-tolyl | | 202° C–205° C |
| 10 | H | H | o-tolyl | HCl | 145° C–150° C |
| 11 | H | H | m-tolyl | | 198° C–201° C |
| 12 | H | H | m-tolyl | HCl | 215° C–220° C (dec) |
| 13 | H | CH$_3$ | m-Chlorophenyl | | 275° C–278° C |
| 14 | H | H | α,α,α-trifluoro-m-tolyl | | 224° C–226° C |
| 15 | H | phenyl | methyl | | 235° C–238° C |
| 16 | H | phenyl | methyl | HCl | 215° C–220° C (dec) |

EXAMPLE 17

Preparation of 4-[182)-Methyl-4-phenyl-3(5)-pyrazolyl]-4H-1,2,4-triazole (isomeric mixture)

4-(4-Phenyl-3-pyrazolyl)-4H-1,2,4-triazole (31.6 g, 0.15 mole) is added to a solution of sodium methoxide (8.0 g, 0.15 mole) in absolute methanol (175 ml.). The mixture is then heated to 55° C for ½ hour and dimethyl sulfate added dropwise. After the addition is complete, the reaction mixture is heated at reflux for 5 hours. The methanol is removed in vacuo and the residual yellow solid extracted with boiling benzene. The benzene solution is treated with charcoal, filtered and cooled. The separated white crystalline solid is filtered and dried in vacuo. Yield 28 g (83%), m.p. 131° C to 135°0 C.

Analysis calculated: C, 63.98; H, 4.92; N, 31.09. Found: C, 63.83; H 4.89; N, 31.09.

The isomeric mixture of the 1(2)-benzyl derivative is prepared by the above procedure using sodium bicarbonate as an acid binder and benzylbromide instead of dimethyl sulfate, m.p. 151° C to 154° C.

EXAMPLE 18

Preparation of 4-(1-Acetyl-4-phenyl-3-pyrazolyl)-4H-1,2,4-triazole

A suspension of 4-(4-phenyl-5-pyrazolyl)-4H-1,2,4-triazole (1.0 g) in acetic anhydride is refluxed until a clear solution is obtained. The solution is poured into ice water and stirred for ½ hour. The yellowish solid is collected and recrystallized from a mixture of chloroform/hexane, giving a white powder, m.p. 165° C to 168° C. Similarly prepared is the propionyl derivative.

EXAMPLE 19

Preparation of 4-[1(2)-N-Methylcarboxamido-4-phenyl 3(5)-pyrazolyl]-4H-1,2,4-triazole (isomeric mixture)

To a solution of 4(4-phenyl-3-pyrazolyl)-4H-1,2,4-triazole in dry dimethylformamide (50 ml) at 150° C. Triethylamine (50 mg) is added and after a few minutes, a white solid begins to form. The reaction mixture is stirred for 18 hours at room temperature. It is then cooled to 15° C, filtered, the isolated solid washed well with water. Crystallization from methanol yields 2.0 g (77%) of white crystals, m.p. 222° C to 225° C.

Analysis calculated: C, 58.19; H, 4.51; N, 31.32. Found: C, 58.06; H, 4.63; N, 31.32.

EXAMPLE 20

The preemergence activity of the compounds of the present invention is demonstrated by the following tests, wherein a 50/50 acetone/water (v/v) mixture and sufficient test compound to provide the amount per hectare of said compound as indicated in Table II when the mixture is applied to pots planted with seeds or propagules of test plant species.

The pots are prepared the day of herbicide treatment by putting 100 ml of soil in each plastic pot as a base, then morningglory and wild oat seeds are placed on this base and covered with 50 ml (1 cm to 1.37 cm) of soil. Seeds of the other 8 plant species identified below are separately mixed with soil and 50 ml of the soil seed mix added to the pot. The pots are then tamped lightly to level the soil and the soil is wetted with water prior to herbicide application. This prewetting insures that the subsequently applied heribicide treatment solution spreads evenly over the surface of the pot and protects the weed seeds from acetone injury. Each of the 10 weed species is contained in a separate pot. The pots are then arranged in 25.4 × 30.4 cm flats prior to chemical treatment.

The planted pots are treated with 5 ml of test solution and then placed on benches in the greenhouse. Pots are watered after treatemtn as needed and held in the greenhouse for 3 weeks at which time the results are recorded, as reported in Table II.

Plant Species Used in Preemergence Herbicide Evaluation

| Common Name | Abbreviation | Scientific Name |
| --- | --- | --- |
| Lambsquarters | LA | Chenopdium album |
| Wild Mustard | MU | Brassica kaber |
| Pigweed | PI | Amaranthus retroflexus |
| Ragweed | RW | Ambrosia artemisiifolia |
| Morningglory | MG | Ipomoea purpurea |
| Barnyardgrass | BA | Echinochloa crusgalli |
| Crabgrass | CR | Digitaria sanguinalis |
| Green Foxtail | FO | Setaria viridis |
| Wild Oats | WO | Avena fatua |
| Velvetleaf | VL | Abutilon theophrasti |
| Corn | CN | Zea mays |
| Cotton | CO | Gossypium virsutum |
| Soybeans | SY | Glycine max |
| Rice | RI | Oryza sativa |

The rating system used in the evaluation of the experimental data is given below:

| Rating System | % Difference in growth from check* |
| --- | --- |
| 0 - No effect | 0 |
| 1 - Possible effect | 1–10 |
| 2 - Slight effect | 11–25 |
| 3 - Moderate effect | 26–40 |
| 5 - Definite injury | 41–60 |
| 6 - Herbicidal effect | 61–75 |
| 7 - Good herbicidal effect | 76–90 |
| 8 - Approaching complete kill | 91–99 |
| 9 - Complete kill | 100 |
| 4 - Abnormal growth, that is, a definite physiological malformation but with an over all effect less than 5 on the rating scale. | |

*Based on visual determination of stand, size, vigor, chlorosis, growth malformation and over-all plant appearance.

TABLE II

| | | Preemergence Herbicidal Activity | | | | | | | | | | | | | |
| --- | --- | --- | --- | --- | --- | --- | --- | --- | --- | --- | --- | --- | --- | --- | --- |
| Compound | Treatment kg/ha | LA | MU | PI | RW | MG | BA | CR | FO | WO | VL | CN | CO | SY | RI |
| 4-(4-p-Chlorophenyl-3-pyrazolyl)-4H-1,2,4-triazole | 11.2 | 9 | 9 | 9 | 9 | 0 | 0 | 0 | 0 | 0 | 7 | | | | |
| 4-(4-Phenyl-3-pyrazolyl-4H-1,2,4-triazole . HCl | 5.6 | 9 | 9 | 9 | 9 | 9 | 9 | 9 | 9 | 9 | 9 | | | | |
| 4-(4-Phenyl-3-pyrazolyl-4H-1,2,4-triazole | 4.5[1] | 9 | 9 | 9 | 9 | 7 | 9 | 9 | 9 | 9 | 9 | 8 | 9 | 9 | 8 |
| 4-(4-Phenyl-3-pyrazolyl-4H-1,2,4-triazole | 0.56[2] | 9 | 9 | 9 | 9 | 5 | 9 | 9 | 8 | 5 | 8 | 2 | 3 | 5 | 1.5 |
| 4-(4-Phenyl-3-pyrazolyl-4H-1,2,4-triazole | 0.28[3] | 9 | 9 | 9 | 7 | 3 | 5 | 7 | 8 | 2 | 5 | 1 | 1 | 1 | 0 |
| 4-(4-Phenyl-3-pyrazolyl-4H-1,2,4-triazole | 0.145[4] | 9 | 8 | 9 | 6 | 1 | 3 | 5 | 6 | 1 | 5 | 0 | 0 | 0 | 0 |
| 4-(1-Acetyl-4-phenyl-3-pyrazolyl)-4H-1,2,4-triazole | 4.5 | 9 | 9 | 9 | 9 | 9 | 9 | 9 | 9 | 9 | 9 | 9 | 9 | 9 | 9 |
| 4-(1-Acetyl-4-phenyl-3-pyrazolyl)-4H-1,2,4-triazole | 0.28 | 9 | 8 | 9 | 9 | 9 | 5 | 6 | 9 | 1 | 3 | 2 | 0 | 0 | 0 |
| 4-(1-Acetyl-4-phenyl-3-pyrazolyl)-4H-1,2,4-triazole . HCl | 5.6 | 9 | 9 | 9 | 9 | 9 | 9 | 9 | 9 | 9 | 9 | | | | |
| 4-(4-p-Fluorophenyl-3-pyrazolyl-4H-1,2,4-triazole | 4.5 | 9 | 9 | 9 | 9 | 9 | 6 | 8 | 8 | 5 | 9 | 1 | 3 | 2 | 3 |
| 4-(4-p-Fluorophenyl-3-pyrazolyl-4H-1,2,4-triazole | 0.56 | 9 | 9 | 9 | 5 | 0 | 0 | 0 | 0 | 0 | 0 | 0 | 0 | 0 | 0 |
| 4-(4-Methyl-5-phenyl-3-pyrazolyl-4H-1,2,4-triazole | 10.1 | 2 | 7 | 7 | 7 | 2 | 2 | 8 | 8 | 2 | 2 | 0 | 0 | 0 | 1 |
| 4-(4-Methyl-5-phenyl-3-pyrazolyl-4H-1,2,4-triazole | 3.35 | 0 | 7 | 5 | 6 | 1 | 1 | 7 | 7 | 0 | 0 | 0 | 0 | 0 | 0 |
| 4-(4-o-Tolyl-3-pyrazolyl)-4H-1,2,4-triazole | 5.6 | 9 | 9 | 9 | 7 | 0 | 0 | 7 | 7 | 0 | 9 | | | | |
| 4-(4-m-Tolyl-3-pyrazolyl)-4H-1,2,4-triazole | 4.5 | 9 | 9 | 9 | 9 | 0 | 6 | 9 | 9 | 6 | 9 | 5 | 0 | 0 | 1 |
| 4-(4-m-Tolyl-3-pyrazolyl)-4H-1,2,4-triazole | 1.12 | 9 | 9 | 9 | 9 | 0 | 0 | 0 | 0 | 0 | 0 | 0 | 0 | 0 | 0 |
| 4-(4-m-Chlorophenyl-5-methyl-3-pyrazolyl)-4H-1,2,4-triazole | 5.6 | 8 | 9 | 8 | 9 | 0 | 0 | 0 | 0 | 0 | 0 | | | | |

TABLE II-continued

| Compound | Treatment kg/ha | Preemergence Herbicidal Activity | | | | | | | | | | | | | |
|---|---|---|---|---|---|---|---|---|---|---|---|---|---|---|---|
| | | LA | MU | PI | RW | MG | BA | CR | FO | WO | VL | CN | CO | SY | RI |
| 4-(4-m-Tolyl-3-pyrazolyl)-4H-1,2,4-triazole . HCl | 11.2 | 9 | 9 | 9 | 9 | 0 | 7 | 9 | 9 | 6 | 9 | | | | |
| 4-(4-o-Tolyl-3-pyrazolyl)-4H-1,2,4-triazole . HCl | 5.6 | 9 | 9 | 9 | 0 | 0 | 0 | 6 | 0 | 5 | 8 | | | | |
| 4-(4-Methyl-5-phenyl-3-pyrazolyl)-4H-1,2,4-triazole . HCl | 11.2 | 0 | 8 | 8 | 7 | 2 | 0 | 8 | 8 | 1 | 2 | | | | |
| 4-(4-m-Chlorophenyl-3-pyrazolyl)-4H-1,2,4-triazole | 11.2 | 9 | 9 | 9 | 9 | 9 | 5 | 7 | 7 | 6 | 3 | | | | |
| 4-(4-m-Chlorophenyl-3-pyrazolyl)-4H-1,2,4-triazole | 4.5 | 9 | 9 | 7 | 9 | 0 | 0 | 0 | 0 | 0 | 0 | 0 | 0 | 0 | 0 |
| 4-(4-m-Fluorophenyl-3-pyrazolyl)-4H-1,2,4-triazole | 4.5 | 9 | 9 | 9 | 9 | 9 | 9 | 9 | 9 | 9 | 9 | 5 | 0 | 0 | 0 |
| 4-(4-m-Fluorophenyl-3-pyrazolyl)-4H-1,2,4-triazole | 0.56 | 9 | 7 | 8 | 9 | 0 | 0 | 0 | 1 | 0 | 2 | 0 | 0 | 0 | 0 |
| 4-(1(2)-Methyl-4-phenyl-3-pyrazolyl)-4H-1,2,4-triazole-isomeric mixture | 4.5 | 9 | 9 | 9 | 9 | 9 | 6 | 9 | 9 | 5 | 8 | 5 | 5 | 6 | 1 |
| 4-(1(2)-Methyl-4-phenyl-3-pyrazolyl)-4H-1,2,4-triazole-isomeric mixture | 1.12 | 8 | 2 | 8 | 9 | 5 | 0 | 1 | 2 | 0 | 2 | 2 | 0 | 0 | 0 |
| 4-(1(2)-Benzyl-4-phenyl-3-pyrazolyl)-4H-1,2,4-triazole-isomeric mixture | 4.5 | 9 | 9 | 9 | 8 | 2 | 7 | 9 | 8 | 5 | 8 | 1 | 0 | 1 | 1 |
| 4-(1(2)-Benzyl-4-phenyl-3-pyrazolyl)-4H-1,2,4-triazole-isomeric mixture | 1.12 | 8 | 1 | 8 | 2 | 0 | 5 | 6 | 6 | 0 | 0 | 1 | 0 | 0 | 0 |
| 4-(1-Propionyl-4-phenyl-3-pyrazolyl)-4H-1,2,4-triazole | 4.5 | 9 | 9 | 9 | 9 | 9 | 9 | 9 | 9 | 9 | 9 | 9 | 9 | 9 | 9 |
| 4-(1-Propionyl-4-phenyl-3-pyrazolyl)-4H-1,2,4-triazole | 1.12 | 9 | 9 | 9 | 9 | 9 | 9 | 9 | 9 | 9 | 9 | 9 | 7 | 9 | 3 |
| 4-(1-Propionyl-4-phenyl-3-pyrazolyl)-4H-1,2,4-triazole | 0.28 | 9 | 9 | 9 | 9 | 3 | 5 | 7 | 9 | 0 | 6 | 2 | 0 | 0 | 0 |
| 4-(4-m-Trifluoromethylphenyl-3-4H-1,2,4-triazole | 4.5 | | 9 | 9 | 8 | 3 | 8 | 9 | 7 | 5 | 7 | 6 | 3 | 3 | 7 |
| 4-(4-Phenyl-3-pyrazolyl)-4H-1,2,4-triazole . HNO₃ | 4.5 | 9 | 9 | 9 | 9 | 2 | 9 | 9 | 9 | 9 | 9 | 6 | 9 | 9 | 8 |
| 4-(4-Phenyl-3-pyrazolyl)-4H-1,2,4-triazole . NHO₃ | 0.56 | 9 | 9 | 9 | 0 | 0 | 7 | 9 | 8 | 1 | 5 | 0 | 0 | 1 | 2 |
| 4-(4-m-Trifluoromethylphenyl-3-pyrazolyl)-4H-1,2,4-triazole | 1.12 | | 9 | 9 | 1 | 1 | 2 | 8 | 1 | 1 | 0 | 2 | 0 | 0 | 1 |
| 4-(1(2)-N-Methylcarboxamide-4-phenyl-3-pyrazolyl)-4H-1,2,4-triazole . isomeric mixture | 11.2 | | 9 | 8 | 5 | 3 | 8 | 9 | 8 | 0 | 5 | | | | |

[1]Average of 4 Replicates
[2]Average of 6 Replicates
[3]Average of 6 Replicates
[4]Average of 5 Replicates

EXAMPLE 21

The postemergence herbicidal activity of the compounds of the present invention is demonstrated by the following tests, wherein a variety of monocotyledonous and dictoyledonous plants are treated with test compounds dispersed in aqueous acetone mixtures. In the tests, seedling plants are grown in jiffy flats for about 2 weeks. The test compounds are dispersed in 50/50 acetone/water (v/v) mixtures containing 0.5% TWEEN® 20, a polyoxyethylene (20) sorbitan monolaurate surfactant by Atlas Chemical Industries, in sufficient quantity to provide the amount per hectare of active compound as indicated in Table III when applied to the plants through a spray nozzle operating at 2.8 kg per cm² pressure for a predetermined time. After spraying, the plants are placed on greenhouse benches and cared for in the usual manner, commensurate with conventional greenhouse practices. Two weeks after treatment, the seeding plants are examined and rated according to the rating system provided in Example 20.

The plant species used in the postemergence herbicide activity evaluation are the same as those used in the preemergence herbicide evaluation test and are listed in Example 20. The results are reported in Table III.

Table III

| Compound | Treatment kg/ha | Postemergence Herbicidal Activity | | | | | | | | | | | | | |
|---|---|---|---|---|---|---|---|---|---|---|---|---|---|---|---|
| | | LA | MU | PI | RW | MG | BA | CR | FO | WO | VL | CN | CO | WY | RI |
| 4-(4-Phenyl-3-pyrazolyl)-4H-1,2,4-triazole . HCl | 5.6 | 9 | 9 | 9 | 9 | 8 | 8 | 8 | 7 | 7 | 6 | | | | |
| 4-(4-Phenyl-3-pyrazolyl)-4H-1,2,4-triazole | 4.5[1] | 9 | 8 | 9 | 5 | 8 | 6 | 7 | 5 | | 5 | 3 | 5 | 6 | 1 |
| 4-(4-Phenyl-3-pyrazolyl)-4H-1,2,4-triazole | 2.24[2] | 8 | 6 | 8 | 2 | 7 | 2 | 3 | 0 | 0 | 3 | 5 | 7 | 7 | 0 |
| 4-(1-Acetyl-4-phenyl-3-pyrazolyl)-4H-1,2,4-triazole | 4.5 | 8 | 8 | 9 | 0 | 7 | 0 | 1 | 1 | 0 | 2 | 5 | 8 | 7 | 0 |
| 4-(1-Acetyl-4-phenyl-3-pyrazolyl)-4H-1,2,4-triazole . HCl | 5.6 | 9 | 9 | 9 | 9 | 7 | 8 | 2 | 6 | 8 | 5 | | | | |
| 4-(4-p-Fluorophenyl-3-pyrazolyl)-4H-1,2,4-triazole | 4.5 | 9 | 8 | 9 | 2 | 3 | 3 | 0 | 0 | 0 | 9 | 0 | 1 | 3 | 0 |
| 4-(4-p-Fluorophenyl-3-pyrazolyl)-4H-1,2,4-triazole | 1.12 | 7 | 5 | 9 | 1 | 1 | 0 | 0 | 0 | 0 | 7 | 0 | 1 | 3 | 0 |
| 4-(4-o-Tolyl-3-pyrazolyl)-4H-1,2,4-triazole | 5.6 | 9 | 9 | 7 | 0 | 0 | 0 | 0 | 0 | 0 | 0 | | | | |
| 4-(4-m-Tolyl-3-pyrazolyl)-4H-1,2,4-triazole | 4.5 | 7 | 9 | 9 | 5 | 7 | 0 | 1 | 0 | 0 | 1 | 1 | 3 | 5 | 0 |
| 4-(4-m-Tolyl-3-pyrazolyl)-4H- | 11.2 | 9 | 9 | 7 | 5 | 1 | 1 | 1 | 1 | 7 | 5 | | | | |

Table III-continued

| Compound | Treatment kg/ha | Postemergence Herbicidal Activity | | | | | | | | | | | | | |
|---|---|---|---|---|---|---|---|---|---|---|---|---|---|---|---|
| | | LA | MU | PI | RW | MG | BA | CR | FO | WO | VL | CN | CO | WY | RI |
| 1,2,4-triazole . HCl 4-(4-m-Chlorophenyl-3-pyrazolyl)-4H-1,2,4-triazole | 11.2 | 9 | 9 | 5 | 0 | 0 | 1 | 1 | 1 | 0 | 0 | | | | |
| 4-(4-m-Fluorophenyl-3-pyrazolyl)-4H-1,2,4-triazole | 11.2 | 8 | 9 | 9 | 9 | 5 | 7 | 6 | 6 | 9 | 5 | | | | |
| 4-(4-Phenyl-3-pyrazolyl)-4H-1,2,4-triazole . HNO$_3$ | 11.2 | 9 | 9 | 9 | 9 | 9 | 9 | 9 | 9 | 9 | 9 | | | | |
| 4-(4-Phenyl-3-pyrazolyl)-4H-1,2,4-triazole . HNO | 1.12 | 9 | 9 | 9 | 2 | 8 | 0 | 2 | 0 | 0 | 5 | 0 | 6 | 5 | 0 |
| 4-(1(2)-Methyl-4-phenyl-3-pyrazolyl)-4H-1,2,4-triazole-isomeric mixture | 11.2 | 9 | 4 | 6 | 0 | 4 | 0 | 0 | 0 | 0 | 2 | | | | |
| 4-(1(2)-Benzyl-4-phenyl-3-pyrazolyl)-4H-1,2,4-triazole, isomeric mixture | 1.12 | 9 | 5 | 5 | 0 | 5 | 0 | 0 | 0 | 0 | 0 | | | | |
| 4-(1-Propionyl-4-phenyl-3-pyrazolyl)-4H-1,2,4-triazole | 11.2 | 9 | 7 | 6 | 1 | 8 | 8 | 7 | 7 | 9 | 8 | | | | |
| 4(1-Propionyl-4-phenyl-3-pyrazolyl)-4H-1,2,4-triazole | 1.12 | 7 | 5 | 7 | 0 | 4 | 4 | 0 | 0 | 5 | 5 | 0 | 7 | 7 | 2 |
| 4(4-m-Trifluoromethylphenyl-3-pyrazolyl)-4H-1,2,4-triazole | 11.2 | 7 | 6 | 8 | 2 | 7 | 2 | 1 | 1 | 0 | 2 | | | | |

[1]Average of 5 Replicate
[2]Average of 2 Replicate

EXAMPLE 22

The aquatic herbicidal activity of the compounds of the present invention is compared to a commercial herbicide: 2-chloro-4-ethylamino-6-isopropylamino-s-triazine, using aquatic weeds as target organisms in the following test, wherein a 50/50 acetone/water (v/v) mixture and sufficient test compound are used to provide the amount per hectare of the compound as indicated in Table IV when the mixture is applied to 5 inch dixie cups planted with propagules of test plant species.

Method

The six species of aquatic weeds:

| Alligator weed | AW | (Alternanthera philoxeroides) |
| Parrot's feather | PF | (Myriophyllum brasiliense) |
| Water hyacinths | WH | (Eichhornia crassipes) |
| Duck weed | DW | (Lemna minor) |
| Salminia | SAL | (Salminia auriculata) |
| Water lettuce | WL | (Pistia stratiotes) | are prepared as follows:

1. Cuttings of alligator weed and parrot's feathers are taken from stock cultures and are set to root in a vermiculite:sand-PERLITE® (1:1:1) mix in shallow flats. A week later, the rooted cuttings are transferred to 5 inch dixie cups ½ filled with coarse sand. The cups are filled to flooding with water and placed in aluminum baking pans.

2. At the same time, the above-rotted cuttings are set in cups, a single propagule of water hyacinth and of water lettuce consisting of stolon, petiole and leafamine are placed in water-filled cups.

3. Also at the same time, enough duck weed and Salminia are transferred from the pond table to their respective cups to cover the surface, and the cups are placed in the aluminum baking pans.

4. The pans with their six cups are placed in the greenhouse and kept at a constant water level and are maintained 4 days prior to spraying.

The plants are sprayed on the fifth day with the test solutions containing the active ingredients in the amounts indicated in Table IV and held in the greenhouse for four weeks. Results are recorded at two and at four weeks as reported in Table IV.

Table IV

Aquatic Herbicidal Activity of a Compound of the Present Invention as Compared to a Commercial Herbicide: 2-Chloro-4-ethylamino-6-isopropylamino-s-triazine at the Indicated Rates.
Two weeks' data, except as indicated.

| Compound | kg/Hectare | AW | PF | WH | DW | SAL | WL |
|---|---|---|---|---|---|---|---|
| 2-Chloro-4-ethylamino-6-isopropylamino-s-triazine | 4.48 | 9 | 9 | 9 | 9 | 9 | 9 |
| | 1.12 | 9 | 9 | 9 | 9 | 9 | 9 |
| | 0.56 | 8 | 9 | 9 | 9 | 9 | 9 |
| | 0.28 | 8 | 8 | 9 | 9 | 9 | 9 |
| 4-(4-Phenyl-5-pyrazolyl)-4H-1,2,4-triazole | 4.48 | 9 | 8 9* | 7 8* | 9 | 5 | 9 |
| | 1.12 | 9 | 7 9* | 2 7* | 9 | 5 | 9 |
| | 0.56 | 9 | 3 8* | 2 5* | 9 | 5 | 9 |
| | 0.28 | 9 | 3 7* | 1 2* | 9 | 5 | 9 |

*Four weeks' data.

We claim:

1. A method for the control of undesirable plant species, comprising contacting the undesirable plant species, seeds or propagules thereof, with a herbicidally effective amount of a compound of the formula:

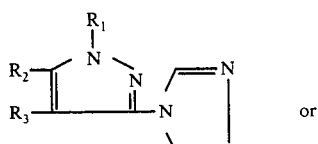 or

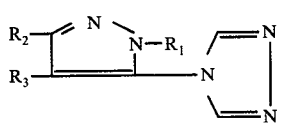

wherein $R_1$ is hydrogen, alkyl ($C_1$-$C_3$), benzyl, acyl RCO wherein R is $C_1$-$C_3$ alkyl or N-alkyl ($C_1$-$C_3$) carboxamido; $R_2$ is hydrogen, methyl or phenyl; $R_3$ is methyl of

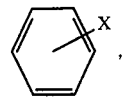

wherein X is hydrogen, halogen, alkyl ($C_1$-$C_3$) or $CF_3$, and the acid addition salt of the compound wherein the acid is HCl, HBr, HI, $HNO_3$, $H_2SO_4$, $HSO_4^-$, $CH_3OSO_2O^-$, $H_3PO_4$, $HClO_3$, alkanoic ($C_2$-$C_4$) acid, benzene sulfonic acid, or p-toluene sulfonic acid.

2. A method according to claim 1 wherein $R_1$ and $R_2$ of the formula are each hydrogen.

3. A method according to claim 1 wherein $R_1$ of the formula is methyl or benzyl; $R_2$ is hydrogen; and $R_3$ is phenyl; and wherein the compound is an isomeric mixture.

4. A method according to claim 1 wherein $R_1$ is acetyl, propionyl or N-methylcarboxamido; $R_2$ is hydrogen; And $R_3$ is phenyl.

5. A method according to claim 1, comprising, contacting the undesirable plant species or seeds thereof with the compound in an amount sufficient to provide from 0.11 kg to 11.2 kg per hectare of the compound.

* * * * *